United States Patent [19]

Nakano et al.

[11] Patent Number: 5,276,041
[45] Date of Patent: Jan. 4, 1994

[54] OXIME DERIVATIVES

[75] Inventors: Jun Nakano; Hideto Fukui; Hisamitsu Haigoh; Hisato Senda; Wakao Iwatani; Tadashi Arika, all of Kyoto, Japan

[73] Assignee: Kaken Pharmaceutical Co., Ltd., Tokyo, Japan

[21] Appl. No.: 972,306

[22] Filed: Nov. 5, 1992

[30] Foreign Application Priority Data

Nov. 8, 1991 [JP] Japan .................................. 3-321067

[51] Int. Cl.$^5$ .................... C07D 401/04; A61K 31/47
[52] U.S. Cl. ..................................... 514/314; 546/156
[58] Field of Search ........................ 546/156; 514/314

[56] References Cited

FOREIGN PATENT DOCUMENTS

| 0230295 | 7/1987 | European Pat. Off. |
| 0326916 | 8/1989 | European Pat. Off. |
| 0357047 | 3/1990 | European Pat. Off. |
| 1-100165 | 4/1989 | Japan . |
| 3-95176 | 4/1991 | Japan . |

OTHER PUBLICATIONS

Chemical Abstract, vol. 111, 1989, AN 153844p, p. 730, Nishitani Yasuhiro, et al., "Preparation of Quinolone-carboxylates and Analogs as Antibacterials".
Journal of Medicinal Chemistry, vol. 35, No. 8, Apr. 1992, pp. 1392-1398, C. S. Cooper, et al., "Preparation and In Vitro and In Vivo Evaluation of Quinolones with Selective Activity Against Gram-Positive Organisms".

Primary Examiner—David B. Springer
Attorney, Agent, or Firm—Oblon, Spivak, McClelland, Maier & Neustadt

[57] ABSTRACT

An oxime derivative of the formula:

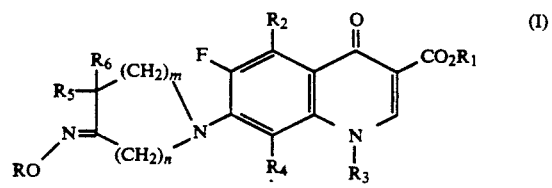

wherein R is a hydrogen atom or a $C_{1-5}$ alkyl group, $R_1$ is a hydrogen atom, a $C_{1-5}$ alkyl group or a carboxyl-protecting group, $R_2$ is a hydrogen atom, a halogen atom, a hydroxyl group or an amino group, $R_3$ is a $C_{3-7}$ cycloalkyl group, $R_4$ is a hydrogen atom, a halogen atom or a $C_{1-4}$ alkoxy group, each of $R_5$ and $R_6$ which may be the same or different, is a hydrogen atom or a $C_{1-5}$ alkyl group, or $R_5$ and $R_6$ together represent a $C_{2-4}$ alkylene group which forms together with the adjacent carbon atom a $C_{3-5}$ ring, provided that when $R_2$ is a hydrogen atom, $R_4$ is a $C_{1-4}$ alkoxy group, m is an integer of 0 or 1, and n is an integer of from 1 to 3; or its pharmaceutically acceptable salt.

12 Claims, No Drawings

OXIME DERIVATIVES

The present invention relates to oxime derivatives. More particularly, it relates to antibacterial oxime derivatives useful as pharmaceuticals, animal drugs, drugs for fisheries, preservatives or industrial antibacterial agents.

Quinolone-type antibacterial agents developed in recent years, such as norfloxacine, ofloxacine, cyprofloxacine and tosfloxacine, have a wide antibacterial spectrum and excellent antibacterial activities against gram positive bacteria and gram negative bacteria, and they are frequently used for the treatment of various infectious diseases.

However, recently, infectious diseases caused by gram positive bacteria such as staphylococcus, have been increasing as a result of common use of third generation cephem-type drugs which have antibacterial activities rather weak against gram positive bacteria, and emergence resistant bacteria such as MRSA (methicillin resistant *Staphylococcus aureus*) has become a serious clinical problem.

Commercially available quinolone-type antibacterial agents have a drawback that they do not have strong antibacterial activities against gram positive bacteria such as storeptococcus or enterococcus, and their antibacterial activities against resistant bacteria such as MRSA are not adequate. Therefore, it has been desired to develop a new compound which has superior antibacterial activities.

Under these circumstances, the present inventors have conducted an extensive research to present an excellent synthetic antibacterial agent which overcome the above-mentioned drawbacks and as a result, have found that oxime derivatives of the following formula (I) and their salts have a wide antibacterial spectrum and exhibit strong antibacterial activities particularly against gram positive bacteria and drug-resistant species thereof, especially against MRSA. The present invention has been accomplished on the basis of this discovery.

The present invention provides an oxime derivative of the formula:

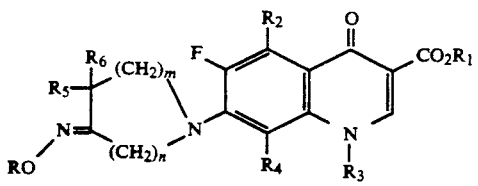

(I)

wherein R is a hydrogen atom or a $C_{1-5}$ alkyl group, $R_1$ is a hydrogen atom, a $C_{1-5}$ alkyl group or a carboxyl-protecting group, $R_2$ is a hydrogen atom, a halogen atom, a hydroxyl group or an amino group, $R_3$ is a $C_{3-7}$ cycloalkyl group, $R_4$ is a hydrogen atom, a halogen atom or a $C_{1-4}$ alkoxy group, each of $R_5$ and $R_6$ which may be the same or different, is a hydrogen atom or a $C_{1-5}$ alkyl group, or $R_5$ and $R_6$ together represent a $C_{2-4}$ alkylene group which forms together with the adjacent carbon atom a $C_{3-5}$ ring, provided that when $R_2$ is a hydrogen atom, $R_4$ is a $C_{1-4}$ alkoxy group, m is an integer of 0 or 1, and n is an integer of from 1 to 3; or its salt.

The compound of the present invention is characterized in that it has strong antibacterial activities specifically against MRSA when it has a structure wherein the cyclic amine residue having an oxime group and substituent $R_3$ at the 1-position of the quinolone structure have $C_{3-7}$ cycloalkyl groups, and particularly when substituent $R_4$ at the 8-position of the quinolone structure is a $C_{1-4}$ alkoxy group or substituent $R_2$ at the 5-position is a fluorine atom, a hydroxyl group or an amino group.

Now, the present invention will be described in detail with reference to the preferred embodiments.

Firstly, the oxime derivative of the formula (I) of the present invention will be described.

In the formula (I), the $C_{1-5}$ alkyl group for R and $R_1$ means a $C_{1-5}$ linear or branched alkyl group, such as a methyl group, an ethyl group, an isopropyl group or a t-butyl group. The carboxyl-protecting group for $R_1$ is an optional alcohol residue of a carboxylate, which can relatively easily be removed to form the corresponding free carboxyl group. Specific examples may be those which can be removed by treatment under mild conditions such as hydrolysis, catalytic reduction or splitting by a transition metal catalyst, for example, a lower alkyl group such as a methyl group, an ethyl group, a n-propyl group or a t-butyl group, a lower alkenyl group such as an allyl group, an aralkyl group such as a benzyl group or a p-methoxybenzyl group, or an aryl group such as a phenyl group, or those which can readily be removed in vivo, for example, a lower alkanoyloxy lower alkyl group such as an acetoxymethyl group, a 1-acetoxyethyl group or a pivaroyloxymethyl group, a lower alkoxycarbonyloxy lower alkyl group such as a methoxycarbonyloxymethyl group or a 1-methoxycarbonyloxyethyl group, a lower alkoxy lower alkyl group such as a methoxymethyl group, a lactonyl group such as a phtharidyl group, or a di-lower alkyl amino lower alkyl group such as a dimethylaminoethyl group.

The halogen atom for $R_2$ and $R_4$ may, for example, be a fluorine atom, a chlorine atom or bromine atom, preferably a fluorine atom or a chlorine atom.

The $C_{3-7}$ cycloalkyl group for $R_3$ may, for example, be a cyclopropyl group, a cyclobutyl group or a cyclopentyl group, preferably a cyclopropyl group.

The $C_{1-4}$ alkoxy group for $R_4$ means a $C_{1-4}$ linear or branched alkoxy group, such as a methoxy group, an ethoxy group or an isopropoxy group, preferably a methoxy group.

The $C_{2-4}$ alkylene group represented by $R_5$ and $R_6$ may, for example, be an ethylene group, a propylene group or a butylene group, which forms together with the adjacent carbon atom a $C_{3-5}$ ring.

There will be geometrical isomers attributable to the oxime group except for a case where both $R_5$ and $R_6$ of the oxime-substituted cyclic amine residue are hydrogen atoms and m and n are 0 and 1, or 1 and 2, respectively. The oxime derivative (I) formed with such a cyclic amine residue as a substituent at the 7-position of the quinolone structure, may sometimes be a mixture of such geometrical isomers. The oxime derivative (I) may be a mixture of optional geometrical isomers, or a pure geometrical isomer such as a trans-form (E-form) or a cis-form (Z-form), unless otherwise specified. The oxime derivative of the present invention may form a base-addition salt. The base-addition salt may, for example, be a salt with an alkali metal such as sodium or potassium, a salt with an alkaline earth metal such as calcium or magnesium, an ammonium salt, a salt with a nitrogen-containing organic base such as a triethylamine, pyridine, N-methylpiperidine, N-methylmorpholine, diethylamine, benzylamine or N,N-dimethylethanolamine.

Now, processes for producing the oxime derivatives of the formula (I) of the present invention will be described. For the production of the compounds of the present invention, suitable processes may be selected for use depending upon e.g. the types of the substituents. However, preferred processes may be shown as follows. In the following description, the following formula will be represented by Q.

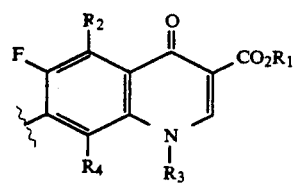

PROCESS 1

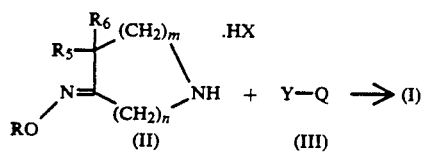

In the above formulas, R, $R_5$, $R_6$, m, n and Q are as defined above, HX represents a mineral acid or an organic acid capable of forming a salt with a basic nitrogen, and Y is a halogen atom.

Y in the above formula (III) may, for example, be a fluorine atom, a chlorine atom or a bromine atom.

The oxime derivative (I) of the present invention can be produced by condensing a cyclic amine (II) having an oxime group with a quinolone derivative (III).

This condensation reaction can be conducted in an aromatic hydrocarbon such as benzene, toluene or xylene, a lower alcohol such as methanol, ethanol or isopropanol, an ether such as tetrahydrofuran, dioxane or monoglime, or an aprotic polar solvent such as acetonitrile, dimethylformamide, dimethyl sulfoxide or sulforane. The reaction temperature is usually from 0° to 200° C., and the reaction time is usually from 10 minutes to 24 hours.

This condensation reaction is conducted usually in the presence of an acid-binding agent using from 1 to 5 equivalent of the cyclic amine (II) relative to the quinolone derivative (III). The acid-binding agent may, for example, be an alkali metal hydroxide such as sodium hydroxide or potassium hydroxide, an alkaline earth metal hydroxide such as calcium hydroxide or magnesium hydroxide, an alkali metal carbonate such as sodium carbonate, sodium hydrogen carbonate, potassium carbonate or potassium hydrogen carbonate, an organic base such as triethylamine, pyridine, N-methylmorpholine or 1,8-diazabicyclo[5,4,0]undeca-7-ene (DBU). The acid-binding agent is used usually in an amount of from 2 to 7 equivalent relative to the quinolone derivative (III), corresponding to the amount of the cyclic amine (II).

PROCESS 2

A compound of the formula (I) wherein $R_1$ is a hydrogen atom can be produced by the following process.

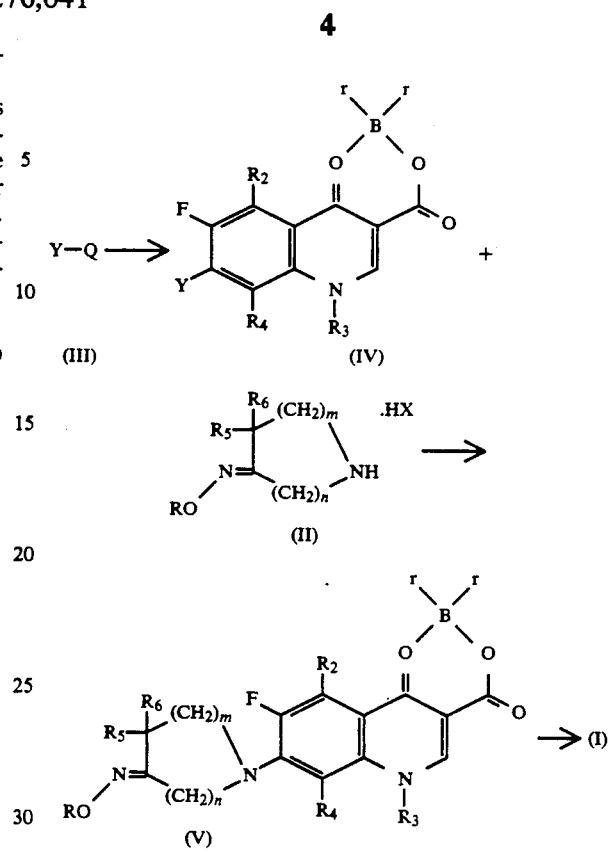

In the above formulas, R, $R_2$, $R_3$, $R_4$, $R_5$, $R_6$, m, n, Y and Q are as defined above, and r is a fluorine atom or an acetoxy group.

In this process, the quinolone derivative (III) is firstly converted to a boron chelate compound (IV), which is then converted by a condensation reaction to a boron chelate product (V), followed by treatment with a base to give the desired compound (I).

The conversion of the quinolone derivative (III) to the boron chelate compound (IV) can be conducted by reacting hydroborofluoric acid, by reacting a boron trifluoride-diethyl ether complex, or by reacting a reagent mixture of boric acid and acetic anhydride.

The amount of the boron reagent to be used, is from 1.2 equivalent to a large excess, relative to the quinolone derivative (III). This chelating reaction is conducted by using an aqueous hydroborofluoric acid solution or an ether-type solvent such as diethyl ether, tetrahydrofuran or dioxane. The reaction is conducted at a temperature of from 20° C. to 100° C., if necessary under heating. The reaction is usually completed in from 30 minutes to 24 hours.

The base to be used for removing the chelate, may, for example, be an alkali metal hydroxide such as sodium hydroxide or potassium hydroxide, an alkaline earth metal hydroxide such as magnesium hydroxide or calcium hydroxide, an alkali metal carbonate such as sodium carbonate or potassium carbonate, or tertiary amine such as triethylamine, trimethylamine or N-methylmorpholine. The base is used usually in an amount of from 2 equivalent to a large excess relative to the boron chelate product (V). This reaction is conducted usually in a water-containing lower alcohol as a solvent, and the reaction is usually completed in from 30 minutes to 12 hours at a temperature of from 20° to 100° C.

PROCESS 3

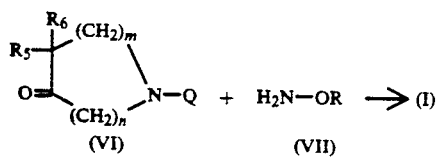

In the above formulas, R, $R_5$, $R_6$, m, n and Q are as defined above.

In this process, a cyclic amine derivative (VI) having a ketone group is condensed with a hydroxyl amine derivative (VII) to give the desired compound (I).

This condensation reaction is completed usually in from 30 minutes to 5 hours at a temperature of from 20° to 100° C. using methanol or ethanol as a solvent.

PROCESS 4

A compound of the formula (I) wherein R is a lower alkyl group, can be produced also by the following process.

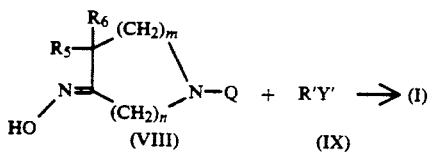

In the above formulas, $R_5$, $R_6$, Q, m and n are as defined above, R' is a lower alkyl group, and Y' is a halogen atom or a sulfonic acid residue.

In the formula (IX), the halogen atom for Y' may, for example, be a chlorine atom, a bromine atom or iodine atom and the sulfonic acid residue for Y' may, for example, be a p-toluene sulfonic acid residue or a 2,4,6-triisopropylbenzene sulfonic acid residue.

In this process, a quinolone derivative (VIII) and the reactant (IX) are condensed to give the desired oxime derivative (I).

This condensation reaction is conducted at a temperature of from 0° to 120° C. for from 30 minutes to 30 hours in the presence of an acid-binding agent such as potassium carbonate, sodium carbonate, triethylamine or pyridine using a lower alcohol such as methanol or ethanol, or an aprotic polar solvent such as acetone, acetonitrile, dimethylformamide or dimethyl sulfoxide as a solvent for the reaction.

PROCESS 5

In this process, an oxime derivative of the formula (I) wherein $R_1$ is a lower alkyl group, is converted to an oxime derivative of the formula (I) in which $R_1$ is a hydrogen atom. This conversion reaction of an ester group to a carboxyl group by hydrolysis can be conducted under either an alkaline condition or an acidic condition.

This conversion reaction can be completed at a temperature of from 0° to 100° C. in from 10 minutes to 5 hours using a basic reactant such as sodium hydroxide, potassium hydroxide, magnesium hydroxide, barium hydroxide or aqueous ammonia and methanol or ethanol as a solvent.

Otherwise, using hydrochloric acid, sulfuric acid, acetic acid, formic acid or a mixture thereof as an acidic reactant and usually a lower alcohol such as methanol, ethanol or isopropanol and water as a solvent, the reaction can be completed at a temperature of from 0° to 130° C., preferably in from 30 minutes to 5 hours.

PROCESS 6

A compound of the formula (I) wherein $R_1$ is a carboxyl-protecting group can be produced also by the following process.

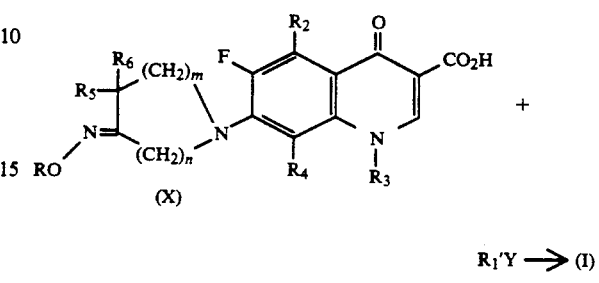

In the formulas, $R'_1$ is a carboxyl-protecting group, and Y, R, $R_2$, $R_3$, $R_4$, $R_5$, $R_6$, m and n are as defined above.

This reaction can be conducted by reacting a halide (XI) to an oxime derivative (X) in the presence of an acid-binding agent.

This reaction can be conducted at a temperature of from 0° to 100° C. for from 30 minutes to 24 hours in the presence of an acid-binding agent such as triethylamine, diisopropylamine, sodium carbonate, potassium carbonate, sodium hydroxide or potassium hydroxide using an aromatic hydrocarbon such as benzene or toluene, a halogenated hydrocarbon such as methylene chloride or chloroform, an aprotic polar solvent such as dimethylformamide or dimethyl sulfoxide, or an ether such as diethyl ether or tetrahydrofuran as a solvent.

The cyclic amine of the formula (II) to be used for these processes for the production of the oxime derivative (I), can be prepared by the following syntheses.

Synthesis a

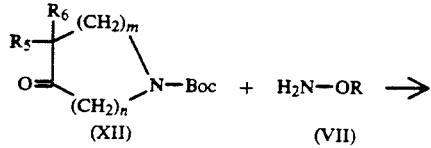

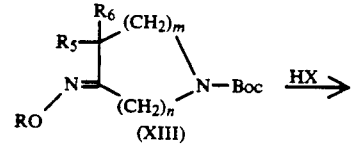

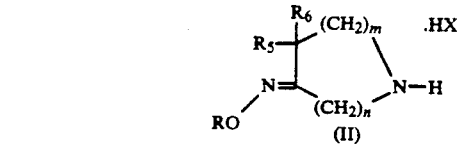

In the above formulas, Boc is a t-butoxycarbonyl group, and R, $R_5$, $R_6$, m, n and HX are as defined above.

An oxocyclic amine (XII) protected by a t-butoxycarbonyl group (hereinafter referred to simply as a Boc group) and a hydroxylamine derivative (VII) are subjected to dehydration condensation in a solvent such as methanol or ethanol at a temperature of from 20° to 100° C. for from 30 minutes to 5 hours to give a protected oxime product (XIII). Then, the product is deprotected by an organic acid or mineral acid such as trifluoroacetic acid or 4N dioxane-hydrochloric acid at a temperature of from −30° to 50° C. for from one minute to one hour to give the desired cyclic amine (II) substituted by an oxime group, in the form of a salt.

Synthesis b

The compound of the above formula (XII) can be obtained by modifying a salt of an oxo-cyclic secondary amine (XIV) with Boc group.

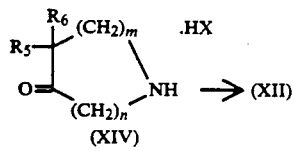

In the above formula, $R_5$, $R_6$, m, n, HX and Boc are as defined above.

Synthesis c

Otherwise, the compound of the formula (XII) can be obtained by modification of a hydroxy-cyclic secondary amine (XV) with Boc group in the same manner as above and following mild oxidation of the resulting hydroxy-N-Boc product (XVI).

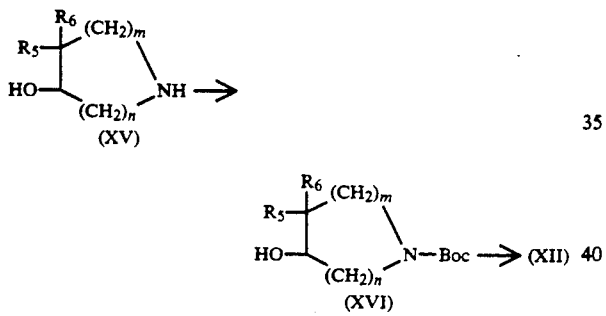

In the above formulas, $R_5$, $R_6$, m, n and Boc are as defined above.

Synthesis d

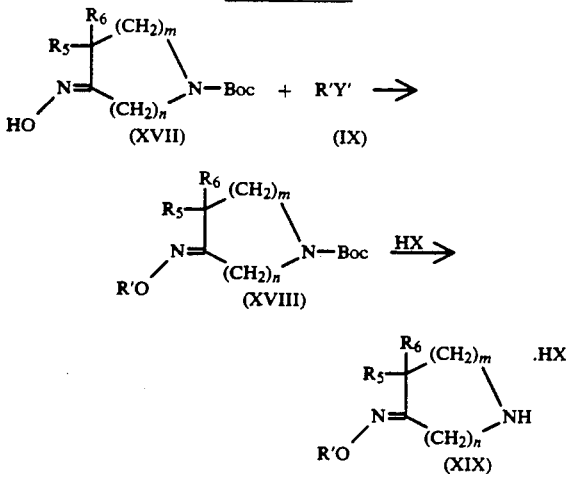

In the above formulas, $R_5$, $R_6$, m, n, Box, R', Y' and HX are as defined above.

The compound (XVII) obtained in the same manner as the above synthesis (a) and a reactant (IX) are condensed at a temperature of from 0° to 120° C. for from 30 minutes to 30 hours in the presence of an acid trapping agent such as potassium carbonate, triethylamine or pyridine using a lower alcohol such as methanol or ethanol, or an aprotic polar solvent such as acetone, acetonitrile, dimethylformamide or dimethyl sulfoxide as the solvent for reaction, to give a compound of the formula (XVIII). Then, in the same manner as in synthesis (a), the Boc group is removed to give the dried cyclic amine (XIX) substituted by an oxime group, in the form of a salt.

The geometrical isomers can be separated and purified in the form of oxime products (XIII) protected by Boc groups, by means of silica gel column chromatography or high performance liquid chromatography. Pure geometrical isomers of the protected oxime products (XIII) thus obtained (E-form and Z-form) can be converted to salts of cyclic amine derivatives each substituted by an oxime group having a desired steric configuration.

The compounds of the present invention have strong antibacterial activities and thus are useful as pharmaceuticals, animal drugs, antibacterial agents for fish, preservatives for food or agricultural chemicals.

When the oxime derivative (I) of the present invention is used as a pharmaceutical, the dose is within a range of from 50 mg to 1 g per day for an adult. This daily dose is administered at once or in a few times per day. However, if necessary, the daily dose is not limited to the above amount. The dose as an animal drug varies depending upon the type and size of the animal or the type of the infectious bacteria, but it is usually within a range of from 1 mg to 200 mg per kilogram of the body weight per day.

The antibacterial agent containing the oxime derivative (I) of the present invention may be formulated into various formulations by common methods with selecting a suitable formulation method depending upon the manner of administration. Namely, the antibacterial agent may be formulated into not only formulations for oral administration such as tablets, powders, granules, capsules, solutions or syrups, but also injection solutions, solid formulations, formulations for external application, eye drops or collunarium.

Now, a Formulation Example will be given below.

FORMULATION EXAMPLE 1

| | |
|---|---|
| Compound of Example 1 | 100 g |
| Cornstarch | 40 g |
| Abicel | 30 g |
| Magnesium stearate | 3 g |

The compound of Example 1, cornstarch, abicel and magnesium stearate were mixed and tabletted to give tablets containing the compound of Example 1 in an amount of 100 mg per tablet.

Now, the present invention will be described in further detail with reference to Examples and Reference Examples. However, it should be understood that the present invention is by no means restricted to such specific Examples.

In these Examples, the $^1$H-NMR spectrum was measured by a spectrometer of JNM-EX270 Model (270 MHz, Nippon Denshi) using tetramethylsilane (TMS) as an internal standard in a $d_6$-dimethyl sulfoxide (DMSO-d6) or deutrated chloroform (CDCl3) solution, and the δ value was shown by ppm. The MS spectrum was measured by a spectrometer of QP1000EX Model (Shimadzu). The melting point was measured by a fine melting point measuring apparatus (manufactured by Yanagimoto) without correction.

REFERENCE EXAMPLE 1

4-hydroxyiminopiperidine trifluoroacetate

The above identified compound can be prepared in accordance with the following formulas.

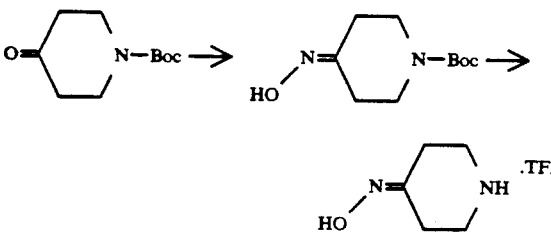

15.5 g (77.6 mmol) of N-Boc-4-piperidone was refluxed for one hour in methanol in the presence of 7.0 g (100.8 mmol) of hydroxylamine hydrochloride and 14.1 ml (100.8 mmol) of triethylamine. Then, methanol was distilled off, and the residue was thoroughly washed with water in chloroform. The chloroform layer was dried over anhydrous magnesium sulfate and then concentrated under reduced pressure to give 10.6 g of N-Boc-4-hydroxyiminopiperidine as white powder.

Melting point: 92°–93° C.
MS(M/Z): 114(M+—Boc), 97(—OH), 85, 69, 56
1H-NMR δ(CDCl3): 1.48(9H,s), 2.32–2.37(2H,m), 2.60–2.64(2H,m), 3.50–3.57(4H,m).

Then, 10.6 g (49.5 mmol) of the above N-Boc-4-hydroxyiminopiperidine was gradually added into 80 ml of trifluoroacetic acid under cooling with ice, and the mixture was stirred at room temperature for 5 minutes. Trifluoroacetic acid was distilled off, and diethyl ether was added to the residue to give 11.0 g of the desired product as colorless powdery crystals.

Melting point: 187°–190° C.
MS(M/Z): 114(M+), 97(M+—OH), 69.
1H-NMR δ(DMSO-d6): 2.44–2.48(2H,m), 2.67–2.71(2H,m), 3.12–3.23(4H,m),9.20(2H,s), 10.81(1H,s).

REFERENCE EXAMPLE 2

4-hydroxyiminopiperidine hydrochloride

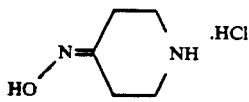

1.54 g (10.0 mmol) of 4-piperidone hydrochloride monohydrate was refluxed for one hour in 30 ml of methanol in the presence of 0.70 g (10.0 mmol) of hydroxylamine hydrochloride and 0.82 g (10.0 mmol) of sodium acetate. Then, methanol was distilled off, and the precipitate thereby formed was washed with isopropanol, and the mother liquor was distilled under reduced pressure. Diethyl ether was added to the residue thereby obtained for crystallization to give 0.45 g of the desired product as colorless powder.

Melting point: 217°–220° C. (Decomposed).
MS(M/Z): 114(M+), 97(M+-OH), 85.
1H-NMR δ(DMSO-d6): 2.46–2.52(2H,m), 2.69–2.73(2H,m), 3.08–3.20(4H,m), 9.45(2H,s), 10.78(1H,s).

REFERENCE EXAMPLE 3

4-methoxyiminopiperidine hydrochloride

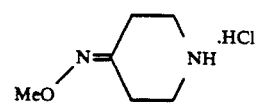

1.59 g of the desired product was obtained as colorless powder in the same manner as in Reference Example 2 except that 0.84 g (10.0 mmol) of O-methylhydroxylamine hydrochloride was used.

Melting point: 138°–140° C.
MS(M/Z): 128(M+), 97(M+—OMe), 82, 68, 56.
1H-NMR δ(CDCl3) 2.69–2.73(2H,m), 2.92–2.97(2H,m), 3.28–3.35(4H,m), 3.85(3H,s), 9.90(2H,s).

REFERENCE EXAMPLE 4

3-hydroxyiminopyrrolidine trifluoroacetate

The above-identified compound was prepared in accordance with the following formulas.

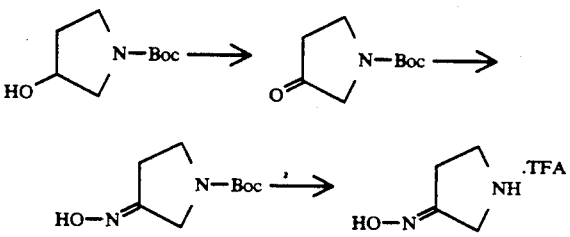

A solution of 5.76 ml of oxalyl chloride in 150 ml of methylene chloride was cooled to −70° C., and a solution of 9.37 ml of DMSO in 36 ml of methylene chloride and a solution of 11.23 g of N-Boc-3-pyrrolidinol in 84 ml of methylene chloride were sequentially added thereto. The mixture was stirred at −70° C. for 15 minutes, and 41.8 ml of triethylamine was added thereto. The mixture was gradually heated to room temperature, and then methylene chloride was distilled off. The obtained precipitate was washed with diethyl ether, and the mother liquor was subjected to silica gel column chromatography with a hexane-diethyl ether-type developer. The eluate was distilled under reduced pressure, and the residue was refluxed for one hour in methanol together with 4.82 g of hydroxylamine hydrochloride and 9.67 ml of triethylamine. Methanol was distilled off, and the precipitate was removed. The mother liquor was washed with water in chloroform. The chloroform layer was dried over anhydrous magnesium sulfate and then distilled under reduced pressure to give 9.23 g of N-Boc-3-hydroxyiminopyrrolidine.

Melting point: 116° C.
MS(M/Z): 200(M+), 145, 127, 111, 100, 83, 57.
1H-NMR δ(CDCl3): 1.48(9H,s), 2.67–2.72(2H,m), 3.60(2H), 4.14(2H,s), 8.68(1H,s)

Then, 4.6 g of the desired product was obtained as colorless powder in the same manner as in Reference Example 1 except that 4.7 g of the above N-Boc 3-hydroxyiminopyrrolidine was used.
Melting point: 145° C.
MS(M/Z): 100(M+), 83(M+-OH), 69.
¹H-NMR δ(DMSO-d₆): 2.59–2.67(2H,m), 3.37–3.45(2H,m), 3.87(2H,s), 9.38(1H,s), 11.17(1H,s).

REFERENCE EXAMPLE 5

3-methoxyiminopyrrolidine hydrochloride

The above-identified compound can be obtained in accordance with the following formulas.

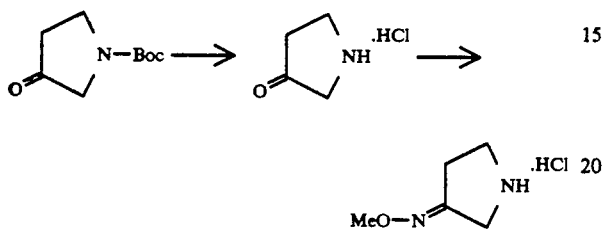

3.0 g of N-Boc-3-pyrrolidone was added to a 4N hydrochloric acid-dioxane solution under cooling with ice. After stirring the mixture at room temperature for 10 minutes, 70 ml of diethyl ether was added thereto. The precipitated crystals were collected by filtration to obtain 1.42 g of 3-pyrrolidone hydrochloride as colorless crystals.
Melting point: 138°–140° C.
MS(M/Z): 85(M+), 69(M+-O).
¹H-NMR δ(DMSO-d₆): 2.50–2.56(2H,m), 3.56–3.62(4H,m), 10.10(2H,s).

Then, 1.49 g of the desired product was prepared in the same manner as in Reference Example 2 except that 1.22 g of (10 mmol) of the above 3-pyrrolidone hydrochloride and 0.84 g (10 mmol) of O-methylhydroxylamine hydrochloride were used.
Melting point: 102° C.
MS(M/Z): 114(M+), 83(M+-OMe), 69, 54.
¹H-NMR δ(DMSO-d₆): 2.61–2.71(2H,m), 3.34–3.42(2H,m), 3.81(3H,s), 3.84(2H,s), 9.91(2H,s).

REFERENCE EXAMPLE 6

A borate of 1-cyclopropyl-6,7-difluoro-8-methoxy-1,4-dihydro-4-oxoquinoline-3-carboxylic acid

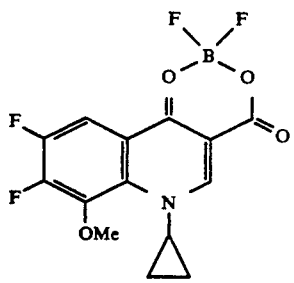

590 mg (2 mmol) of 1-cyclopropyl-6,7-difluoro-8-methoxy-1,4-dihydro-4-oxoquinoline-3-carboxylic acid was suspended in 13 ml of 42% hydrofluoroboric acid. The mixture was stirred at 100° C. for 3 hours and then poured into water. The precipitate thereby formed was collected by filtration, and recrystallized from acetone diethyl ether to give 432 mg of the desired borate as colorless powder.
Melting point: 220°–225° C.
MS(M/Z): 344(M+), 299, 250.
¹H-NMR δ(DMSO-d₆): 1.28–1.38(4H,m), 4.17(3H,s), 4.49–4.56(1H,m), 8.24–8.31(1H,dd,J=8.25,9.90), 9.19(1H,s).

EXAMPLE 1

1-cyclopropyl-6-fluoro-1,4-dihydro-7-(4-hydroxyimino-1-piperidinyl)-8-methoxy-4-oxoquinoline-3-carboxylic acid

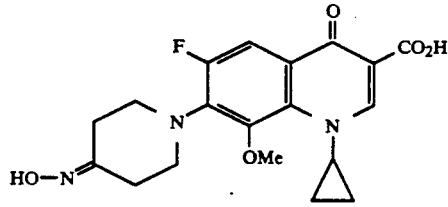

343 mg (1 mmol) of the borate obtained in Reference Example 6 was dissolved in 5 ml of dimethyl sulfoxide, and 456 mg (2 mmol) of 4-hydroxyiminopiperidinetrifluoroacetate and 303 mg (3 mmol) of triethylamine were added thereto. The mixture was stirred at room temperature for 10 hours. The reaction solution was poured into water, and the yellow precipitate thereby formed, was collected by filtration. The precipitate was suspended in a mixture of 100 ml of 80% ethanol and 17 ml of triethylamine, and the suspension was refluxed under heating for 1.5 hours. The reaction solution was concentrated under reduced pressure, and the residue was washed with isopropanol and put on a filter paper and washed with diethyl ether to give 282 mg of the desired compound as slightly yellow powder.
Melting point: 258°–261° C. (Decomposed).
MS(M/Z): 389(M+), 346, 330, 287, 245.
¹H-NMR δ(DMSO-d₆): 1.03–1.21(4H,m), 2.41–2.46(2H,m), 2.66–2.70(2H,m), 3.33–3.45(4H,m), 3.77(3H,s), 4.14–4.20(1H,m), 7.77(1H,d,J=12.2Hz), 8.71(1H,s), 10.49(1H,s), 14.94(1H,s).

REFERENCE EXAMPLE 7

1-cyclopropyl-6-fluoro-1,4-dihydro-8-methoxy-7-(4-oxo-1-piperidinyl)-4-oxoquinoline-3-carboxylic acid

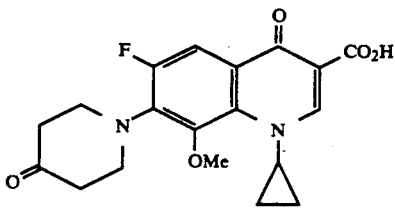

180 mg of the desired compound was obtained as pale yellow powder in the same manner as in Example 1 except that 241 mg (2 mmol) of 4-piperidone hydrochloride was used.
Melting point: 209°–210° C. (Decomposed).
MS(M/Z): 374(M+), 330, 246.
¹H-NMR δ(CDCl₃): 1.00–1.06(2H,m), 1.20–1.29(2H,m), 2.56–2.69(4H,m), 3.70–3.74(4H,m), 3.82(4H,s), 4.01–4.10(1H,m), 7.93(1H,d,J=11.9Hz), 8.84(1H,s), 14.67(1H,s).

EXAMPLE 2

1-cyclopropyl-6-fluoro-1,4-dihydro-8-methoxy-7-(4-methoxyimino-1-piperidinyl)-4-oxoquinoline-3-carboxylic acid

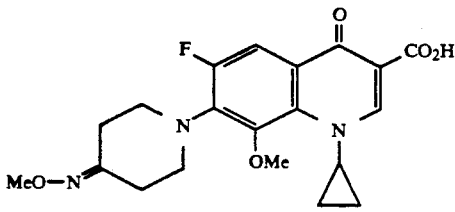

124 mg (0.33 mmol) of a ketone product obtained in Reference Example 7 was dissolved in a solvent mixture of 10 ml of methanol and 6 ml of chloroform, and 33 mg of O-methylhydroxylamine hydrochloride and 50 mg of triethylamine were added thereto. The mixture was refluxed for one hour. The reaction solution was concentrated under reduced pressure, and the precipitate thereby formed was collected by filtration and washed with methanol and then diethyl ether to give 67 mg of the desired product as pale yellow powder.

Melting point: 185°-187° C. (Decomposed).
MS(M/Z) 403(M+), 359,245.
$^1$H-NMR $\delta$(CDCl$_3$): 0.98–1.04(2H,m), 1.20–1.27(2H,m), 2.51–2.55(2H,m), 2.76–2.80(2Hm,), 3.45–3.56(4H,m), 3.78(3H,s), 3.88(3H,s), 3.99–4.08(1H,m), 7.89(1H,d,J=12.3Hz), 8.82(1H,s), 14.74(1H,s).

EXAMPLE 3

5-amino-1-cyclopropyl-6,8-difluoro-1,4-dihydro-7-(4-hydroxyimino-1-piperidinyl)-4-oxoquinoline-3-carboxylic acid

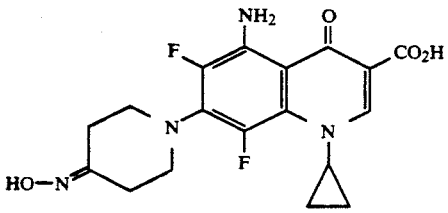

298 mg (1 mmol) of 5-amino-1-cyclopropyl-6,7,8-trifluoro-1,4-dihydro-4-oxoquinoline-3-carboxylic acid was dissolved in 5 ml of dimethyl sulfoxide, and 570 mg (2.5 mmol) of 4-hydroxyiminopiperidine-trifluoroacetate and 404 mg (4 mmol) of triethylamine were added thereto. The mixture was stirred at 80° C. for 6 hours. After cooling, the precipitate thereby formed was collected by filtration and washed with water, isopropanol and diethyl ether to give 150 mg of the desired product as yellow powder.

Melting point: 298°-300° C. (Decomposed).
MS(M/Z): 392(M+), 295,242.
$^1$H-NMR $\delta$(DMSO-d$_6$): 1.10–1.13(4H,m), 2.34–2.39(2H,m), 2.62–2.66(2H,m), 3.37–3.44(4H,m), 4.02–4.04(1H,m), 7.27(2H,brs), 8.52(1H,s), 10.48(1H,s), 14.69(1H,s).

REFERENCE EXAMPLE 8

5-amino-1-cyclopropyl 6,8-difluoro-7-(4-oxo-1-piperidinyl)-1,4-dihydro-4-oxoquinoline-3-carboxylic acid

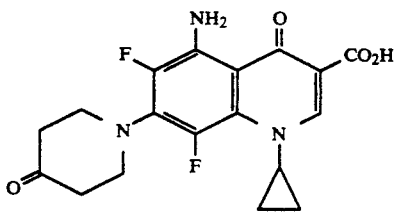

173 mg of the desired product was obtained as yellow powder in the same manner as in Example 3 except that 301 mg (2.5 mmol) of 4-piperidone hydrochloride was used as the starting material.

Melting point: 265°-268° C. (Decomposed).
MS(M/Z): 377(M+), 333, 256.
$^1$H-NMR $\delta$(DMSO-d$_6$) 1.07–1.11(4H,brs), 2.51–2.55(4H,m), 3.53–3.65(4H,m), 4.01–4.04(1H,m), 7.31(2H,brs), 8.52(1H,s), 14.66(1H,s).

EXAMPLE 4

5-amino-1-cyclopropyl-6,8-difluoro-1,4-dihydro-7-(4-methoxyimino-1-piperidinyl)-4-oxoquinoline-3-carboxylic acid

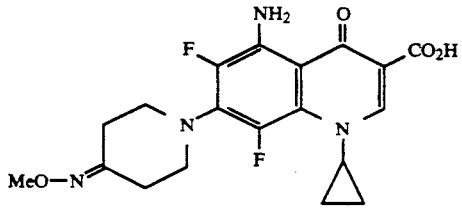

100 mg of the desired product was obtained as yellow powder in the same manner as in Example 2 except that 125 mg (0.33 mmol) of the ketone product obtained in Reference Example 8 was used.

Melting point: 238°-239° C. (Decomposed).
MS(M/Z): 406(M+), 376, 242.
$^1$H-NMR $\delta$(CDCl$_3$): 1.07–1.09(2H,brs), 1.19–1.27(2H,m), 2.48–2.52(2H,m), 2.73–2.77(2H,m), 3.41–3.52(4H,m), 3.87(3H,s), 3.90–3.96(1H,m), 6.50(2H,brs), 8.65(1H,s), 14.61(1H,s).

EXAMPLE 5

1-cyclopropyl-5,6,8-trifluoro-1,4-dihydro-7-(4-hydroxyimino-1-piperidinyl)-4-oxoquinoline-3-carboxylic acid

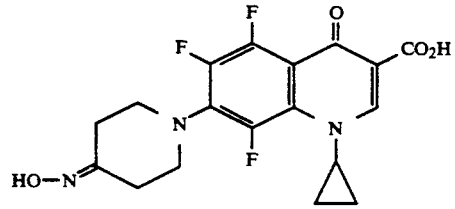

260 mg of the desired product was obtained as pale yellow powder by conducting the reaction at 80° C. for 15 hours in the same manner as in Example 3 except that 301 mg of 1-cyclopropyl-5,6,7,8-tetrafluoro-1,4-dihydro-4-oxoquinoline-3-carboxylic acid was used as the starting material and 15 ml of acetonitrile was used as the solvent for reaction.

Melting point: 330° C.
MS(M/Z): 395(M+), 351, 293, 254.
¹H-NMR δ(DMSO-d₆): 1.10–1.15(4H,m), 2.40–2.44(2H,m), 2.65–2.69(2H,m), 3.37–3.51(4H,m), 4.10(1H,brs), 8.66(1H,s), 10.52(1H,s), 14.63(1H,s).

EXAMPLE 6

1-cyclopropyl-6,8-difluoro-1,4-dihydro-5-hydroxy-7-(4-hydroxyimino-1-piperidinyl)-4-oxoquinoline-3-carboxylic acid

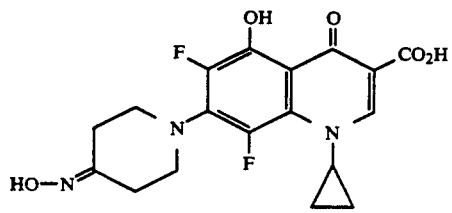

253 mg of the desired product was obtained as pale yellow powder by conducting the reaction at 50° C. for 12 hours in the same manner as in Example 3 except that 299 mg (1 mmol) of 1-cyclopropyl-6,7,8-trifluoro-1,4-dihydro-5-hydroxy-4-oxoquinoline-3-carboxylic acid was used as the starting material.

Melting point: 285°–289° C. (Decomposed).
MS(M/Z): 393(M+), 336, 291.
¹H-NMR δ(DMSO d₆): 1.15–1.24(4H,m), 2.35–2.43(2H,m), 2.60–2.67(2H,m), 3.39–3.48(4H,m), 4.06–4.12(1H,m), 8.62(1H,s), 10.49(1H,s), 13.16(1H,brs), 13.34(1H,s).

REFERENCE EXAMPLE 9

1-cyclopropyl-6,8-difluoro-1,4-dihydro-5-hydroxy-7-(4-oxo-1-piperidinyl)-4-oxoquinoline-3-carboxylic acid

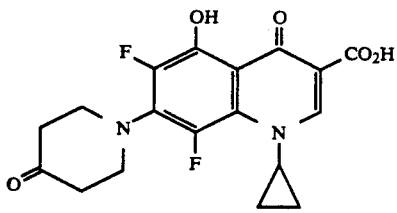

302 mg of the desired product was obtained as yellow powder in the same manner as in Example 6 except that 301 mg (2.5 mmol) of 4-piperidone hydrochloride was used as the starting material.

Melting point: 289°–293° C. (Decomposed).
MS(M/Z): 378(M+), 334, 257.
¹H-NMR δ(CDCl₃): 1.17–1.36(4H,m), 2.64–2.68(4H,m), 3.70–3.74(4H,m), 3.96–4.06(1H,m), 8.76(1H,s), 12.88(1H,s), 13.31(1H,s).

EXAMPLE 7

1-cyclopropyl-6,8-difluoro-1,4-dihydro-5-hydroxy-7-(4-methoxyimino-1-piperidinyl)-4-oxoquinoline-3-carboxylic acid

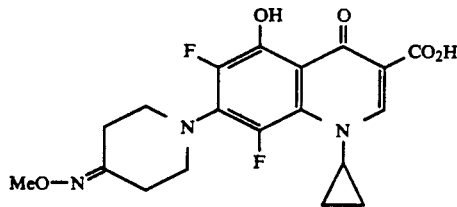

116 mg of the desired product was obtained as yellow powder in the same manner as in Example 2 except that 126 mg (0.33 mmol) of the ketone product obtained in Reference Example 9 was used as the staring material.

Melting point: 204°–205° C. (Decomposed).
MS(M/Z): 407(M+), 363, 338.
¹H-NMR δ(CDCl₃): 1.16–1.25(2H,m), 1.27–1.34(2H,m), 2.49–2.54(2H,m), 2.74–2.79(2H,m), 3.46–3.57(4H,m), 3.87(3H,s), 3.94–4.05(1H,m), 8.74(1H,s), 12.85(1H,s), 13.38(1H,s).

EXAMPLE 8

1-cyclopropyl-6-fluoro-1,4-dihydro-7-(3-hydroxyimino-1-pyrrolidinyl)-8-methoxy-4-oxoquinoline-3-carboxylic acid

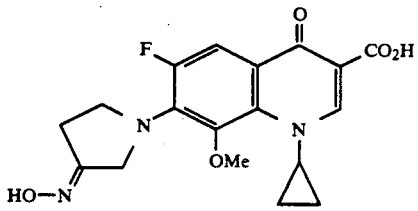

To 343 mg (1 mmol) of the borate obtained in Reference Example 6, 428 mg (2 mmol) of 3-hydroxyiminopyrrolidine-trifluoroacetate was reacted at room temperature for 16 hours in the same manner as in Example 1 and then the boron chelate was removed in the same manner as in Example 1 to give 250 mg of the desired product as slightly yellow powder.

Melting point: 239°–242° C. (Decomposed).
MS(M/Z): 375(M+), 331, 301.
¹H-NMR δ(DMSO-d₆): 1.02–1.15(4H,m), 2.67–2.75(2H,m), 3.64(3H,s), 3.76–3.82(2H,m), 4.13–4.25(3H,m), 7.72(1H,d,J=13.2Hz), 8.69(1H,s), 10.78(1H,s), 15.00(1H,s).

EXAMPLE 9

1-cyclopropyl-6-fluoro-1,4-dihydro-8-methoxy-7-(3-methoxyimino-1-pyrrolidinyl)-4-oxoquinoline-3-carboxylic acid

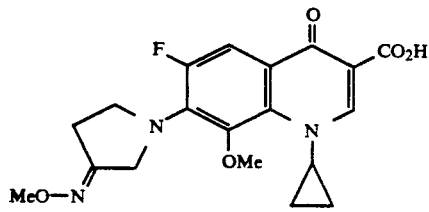

To 343 mg (1 mmol) of the borate obtained in Reference Example 6, 300 mg (2 mmol) of 3-methoxyiminopyrrolidine hydrochloride was reacted at room temperature for 19 hours in the same manner as in Example 1, and then the obtained borate was treated in the same manner as in Example 1 to give 220 mg of the desired product as pale yellow powder.

Melting point: 202°–203° C. (Decomposed).
MS(M/Z): 389(M+), 345, 300, 245.
$^1$H NMR δ(DMSO-$d_6$): 1.00–1.22(4H,m), 2.71$_{2.77}$(2H,m), 3.65(3H,s), 3.77–3.81(2H,m), 3.83(3H,s), 4.13–4.26(3H,m), 7.72(1H,d,J=13.5Hz), 8.70(1H,s), 14.94(1H,brs).

EXAMPLE 10

5-amino-1-cyclopropyl-6,8-difluoro-1,4-dihydro-7-(3-hydroxyimino-1-pyrrolidinyl)-4-oxoquinoline-3-carboxylic acid

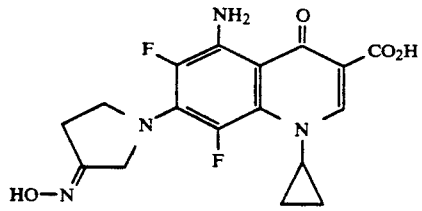

298 mg of 5-amino-1-cyclopropyl-6,7,8-trifluoro-1,4-dihydro-4-oxoquinoline-3 -carboxylic acid 535 mg of 3-hydroxyiminopyrrolidine-trifluoroacetate and 404 mg of triethylamine were reacted at 80° C. for 15 hours using as a solvent a mixture of 5 ml of dimethyl sulfoxide and 15 ml of acetonitrile. After cooling, the precipitate thereby formed was collected by filtration and recrystallized from a mixture of 10 ml of dimethyl sulfoxide and 15 ml of isopropanol to give 210 mg of the desired product as yellow powder.

Melting point: 273–276° C. (Decomposed).
MS(M/Z): 378(M+), 360, 347, 242.
$^1$H-NMR δ(DMSO-$d_6$): 1.03–1.12(4H,m), 2.64–2.71(2H,m), 3.82(2H,brs), 4.00–4.02(1H,m), 4.29(2H,s), 7.23(2H,brs), 8.31(1H,s), 10.79(1H,s), 14.75(1H,s).

EXAMPLE 11

5-amino-1-cyclopropyl-6,8-difluoro-1,4-dihydro-7-(3-methoxyimino-1-pyrrolidinyl)-4-oxoquinoline-3-carboxylic acid

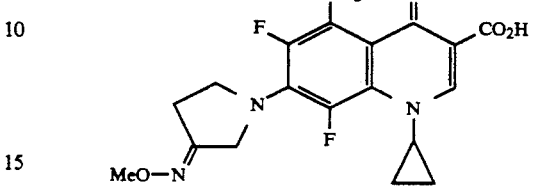

325 mg of the desired product was obtained as yellow powder by conducting the reaction at 60° C. for 3 hours in the same manner as in Example 3 except that 298 mg (1 mmol) of 5-amino-1-cyclopropyl-6,7,8-trifluoro-1,4-dihydro-4-oxoquinoline-3-carboxylic acid and 375 mg of (2.5 mmol) of 3-methoxyiminopyrrolidine hydrochloride were used as the starting materials.

Melting point: 230°–231° C. (Decomposed).
MS(M/Z): 392(M+), 277, 242.
$^1$H-NMR δ(DMSO-$d_6$): 1.03–1.16(4H,m), 2.68–2.73(2H,m), 3.81–3.82(5H,brs), 3.99–4.03(1H,m), 4.29(2H,s), 7.22(2H,brs), 8.49(1H,s), 14.73(1H,s).

EXAMPLE 12

1-cyclopropyl-5,6,8-trifluoro-1,4-dihydro 7-(3-hydroxyimino-1-pyrrolidinyl)-4-oxoquinoline-3-carboxylic acid

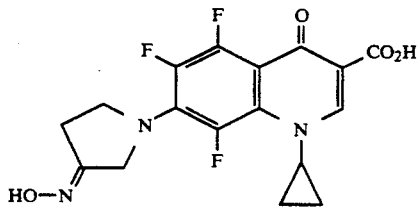

The reaction was conducted at room temperature for 3 hours in the same manner as in Example 3 except that 300 mg (1 mmol) of 1-cyclopropyl-5,6,7,8-tetrafluoro-1,4-dihydro-4-oxoquinoline-3-carboxylic acid and 535 mg (2.5 mmol) of 3-hydroxyiminopyrrolidine-trifluoroacetate were used as starting materials and 5 ml of dimethyl sulfoxide was used as the solvent for reaction. 7 ml of isopropanol was added to the reaction mixture, and the precipitate thereby formed was collected by filtration and recrystallized from a mixture of 6 ml of dimethyl sulfoxide and 6 ml of isopropanol to give 170 mg of the desired product as pale yellow powder.

Melting point: 300° C.
MS(M/Z): 381(M+), 337.
$^1$H-NMR δ(DMSO-$d_6$): 1.13(4H,brs), 2.67–2.75 (2H,m), 3.90–3.95(2H,m), 4.08–4.10(1H,m), 4.38(2H,s), 8.62(1H,s), 10.87(1H,s), 14.78(1H,s).

EXAMPLE 13

1-cyclopropyl-6,8-difluoro-1,4-dihydro-5-hydroxy-7-(3-hydroxyimino-1-pyrrolidinyl)-4-oxoquinoline-3-carboxylic acid

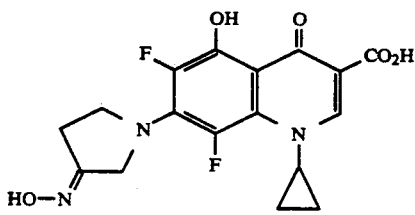

283 mg of the desired product was obtained as pale yellow powder by conducting the reaction at 50° C. for 12 hours in the same manner as in Example 3 except that 299 mg (1 mmol) of 3-cyclopropyl-6,7,8-trifluoro-1,4-dihydro-5-hydroxy-4-oxoquinoline-3-carboxylic acid and 535 mg (2.5 mmol) of 3-hydroxyiminopyrrolidine-trifluoroacetate were used as the staring materials.

Melting point: 270°-272° C. (Decomposed).
MS(M/Z): 379(M+), 336, 263.
$^1$H-NMR  $\delta$(DMSO-d$_6$):  1.15-1.17(4H,m), 2.65-2.73(2H,m), 3.86-3.88(2H,m), 4.04-4.10(1H,m), 4.34(2H,s), 8.60(1H,s), 10.83(1H,s), 13.24(1H,s).

REFERENCE EXAMPLE 10

7-hydroxyimino-5-azaspiro[2,4]heptane trifluoroacetate

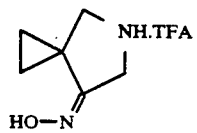

12.5 g of the desired product was obtained as white powder in the same manner as in Reference Example 1 except that 16.4 g (77.6 mmol) of N-Boc-7-oxo-5azaspiro[2,4]heptane was used.

Melting point: 119°-121° C.
MS(M/Z): 126(M+), 110, 69.
$^1$H-NMR $\delta$(DMSO-d$_6$): 0.97-1.07(4H,m), 3.41(2H,s), 4.06(2H,s), 9.71(2H,s), 11.00(1H,s).

REFERENCE EXAMPLE 11

7-methoxyimino-5-azaspiro[2,4]heptane trifluoroacetate

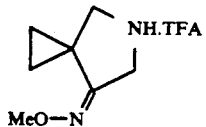

12.8 g of the desired product was obtained as oil in the same manner as in Reference Example 1 except that 16.4 g (77.6 mmol) of N-Boc-7-oxo-5-azaspiro[2,4]heptane and 8.4 g (100 mmol) of O-methylhydroxyamine hydrochloride were used.

MS(M/Z): 139(M+-1), 109, 55.
$^1$H-NMR  $\delta$(DMSO-d$_6$)  1.02-1.14(4H,m), 3.41(2H,brs), 3.76(3H,s), 4.08(2H,brs), 9.54(2H,brs).

EXAMPLE 14

1-cyclopropyl-6-fluoro-1,4-dihydro-7-(7-hydroxyimino-5-azaspiro[2,4]heptan-5-yl)-8-methoxy-4-oxoquinoline-3-carboxylic acid

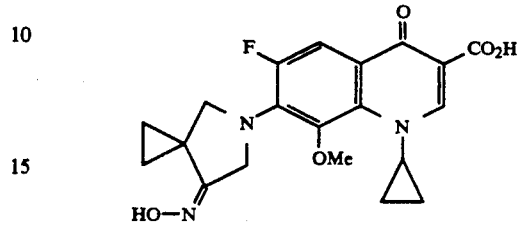

To 343 mg (1 mmol) of the borate obtained in Reference Example 6, 480 mg (2 mmol) of 7-hydroxyimino-5azaspiro[2,4]heptane trifluoroacetate was reacted at room temperature for 15 hours in the same manner as in Example 1, and the obtained borate was treated in the same manner as in Example 1 to give 280 mg of the desired product as pale yellow powder.

Melting point: 233°-235° C. (Decomposed).
MS(M/Z): 401(M+), 357, 245.
$^1$H-NMR $\delta$(DMSO-d$_6$): 1.04-1.17(8H,m), 3.68(3H,s), 3.81(2H,s), 4.15-4.20(1H,m), 4.45(2H,s), 7.73(1H,d,J=13.5Hz), 8.70(1H,s), 10.62(1H,s), 14.98(1H,brs).

EXAMPLE 15

1-cyclopropyl-6-fluoro-1,4-dihydro-8-methoxy-7-(7-methoxyimino-5-azaspiro[2,4]heptan-5-yl)-4-oxoquinoline-3-carboxylic acid

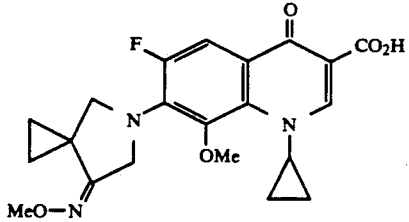

To 343 mg (1 mmol) of the borate obtained in Reference Example 6, 508 mg (2 mmol) of 7-methoxyimino-5-azaspiro[2,4]heptane trifluoroacetate was reacted at room temperature for 18 hours in the same manner as in Example 1, and then the obtained borate was treated in the same manner as in Example 1 to give 266 mg of the desired product as pale yellow powder.

Melting point: 219°-221° C. (Decomposed).
MS(M/Z): 415(M+), 371, 259.
$^1$H-NMR $\delta$(DMSO-d$_6$): 1.00-1.14(8H,m), 3.66(3H,s), 3.76(3H,s), 3.81(2H,s), 4.13-4.21(1H,m), 4.46(2H,s), 7.12(1H,d,J=13.2Hz), 8.69(1H,s), 14.97(1H,brs).

EXAMPLE 16

5-amino-1-cyclopropyl-6,8-difluoro-1,4-dihydro-7-(7-hydroxyimino-5-azaspiro[2,4]heptan-5-yl)-4-oxoquinoline- 3-carboxylic acid

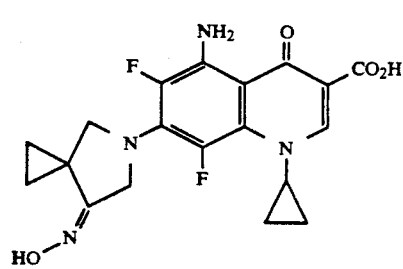

390 mg of the desired product was obtained as yellow powder in the same manner as in Example 3 except that 600 mg (2.5 mmol) of 7-hydroxyimino-5-azaspiro[2,4-]heptane trifluoroacetate was used as the starting material.

Melting point: 261°–262° C. (Decomposed).

MS(M/Z): 404(M+), 303, 242.

1H-NMR δ(DMSO d6): 1.00–1.12(8H,m), 3.86(2H,s), 4.00–4.02(1H,m), 4.48(2H,s), 7.21(2H,brs), 8.49(1H,s), 10.64(1H,s), 14.75(1H,s).

EXAMPLE 17

5-amino-1-cyclopropyl-6,8-difluoro-1,4-dihydro-7-(7-methoxyimino-5-azaspiro[2,4]heptan-5-yl)-4-oxoquinoline-3-carboxylic acid

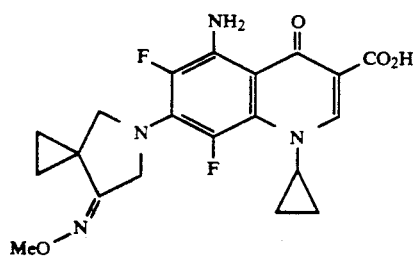

349 mg of the desired product was obtained as yellow powder in the same manner as in Example 3 except that 635 mg (2.5 mmol) of 7-methoxyimino-5-azaspiro[2,4-]heptane trifluoroacetate was used as the starting material.

Melting point: 278°–280° C. (Decomposed).

MS(M/Z): 418(M+), 303, 242.

1H-NMR δ(DMSO-d6): 1.03–1.10(8H,m), 3.75(3H,s), 3.85(2H,s), 3.98–4.02(1H,m), 4,49(2H,s), 7.22(2H,brs), 8.50(1H,s), 14.72(1H,brs).

REFERENCE EXAMPLE 12

1-cyclopropyl-6-fluoro-1,4-dihydro-7-(4,4-dimethyl-2-aza-6,9-dioxaspiro[4,4]nonan-2-yl)-8-methoxy-4-oxoquinoline-3-carboxylic acid

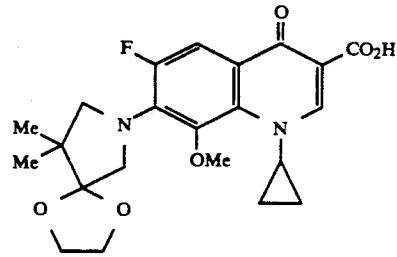

To 343 mg (1 mmol) of the borate obtained in Reference Example 6, 542 mg (2 mmol) of 4,4-dimethyl-2-aza-6,9-dioxaspiro[4,4]nonane trifluoroacetate was reacted at room temperature for 17 hours in the same manner as in Example 1, and then the obtained borate was treated in the same manner as in Example 1 to give 320 mg of the desired product as colorless powder.

Melting point: 213°–216° C.

MS(M/Z): 432(M+), 388, 274.

1H-NMR δ(DMSO-d6): 1.00–1.14(4H,m), 1.11(6H,s), 3.55(2H,s), 3.56(3H,s), 3.64(2H,s), 3.97(4H,s), 4.08–4.16(1H,m), 7.64(1H,d,J=13.8Hz), 8.66(1H,s), 15.08(1H,s).

REFERENCE EXAMPLE 13

1-cyclopropyl-6-fluoro-1,4-dihydro-8-methory-7-(3,3-dimethyl-4-oxopyrrolidinyl)-4-oxoquinoline-3-carboxylic acid

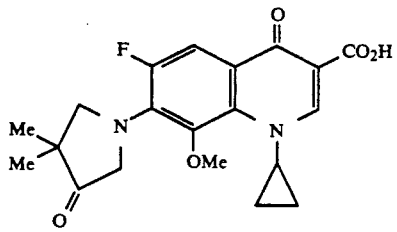

350 mg of 1-cyclopropyl-6-fluoro-1,4-dihydro-7-(4,4-dimethyl-2-aza-6,9-dioxaspiro[4,4]nonan-2-yl)-8-methoxy-4-oxoquinoline-3-carboxylic acid obtained in Reference Example 12 was dissolved in 4 ml of DMSO and 10 ml of methanol, and 7 ml of 6N hydrochloric acid was added thereto. The mixture was stirred at 70° C. for 30 minutes. The reaction solution was poured into 50 ml of ice water, and the precipitate thereby formed was collected by filtration and washed with isopropanol and diethyl ether to give 300 mg of the desired product as pale yellow powder.

Melting point: 215°–219° C.

MS(M/Z): 388(M+), 344, 260.

1H-NMR δ(DMSO-d6): 0.95–1.17(4H,m), 1.19(6H,s), 3.68(3H,s), 3.81(2H,s), 4.10(2H,s), 4.11–4.19(1H,m), 7.73(1H,d,J=13.8Hz), 8.70(1H,s), 14.94(1H,s).

EXAMPLE 18

1-cyclopropyl-6-fluoro-1,4-dihydro-7-(3-hydroxyimino-4,4-dimethylpyrrolidinyl)-8-methoxy-4-oxoquinoline-3-carboxylic acid

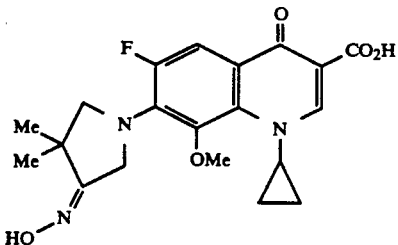

95 mg of the desired product was obtained as colorless powder in the same manner as in Example 2 except that 124 mg (0.33 mmol) of the ketone product obtained in Reference Example 13 and 30 mg of hydroxylamine hydrochloride as the starting material.

Melting point: 247°-249° C. (Decomposed).

MS(M/Z): 403(M+), 359.

$^1$H-NMR δ(DMSO-d$_6$): 1.02–1.17(4H,m), 1.28(6H,s), 3.60(2H,s), 3.65(3H,s), 4.12–4.20(1H,m), 4.34(2H,s), 7.73(1H,d,J=13.7Hz), 8.70(1H,s), 10.76(1H,s), 14.98(1H,s).

EXAMPLE 19

1-cyclopropyl-6-fluoro-1,4-dihydro-8-methoxy-7-(3-methoxyimino-4,4-dimethylpyrrolidinyl)-4-oxoquinoline-3-carboxylic acid

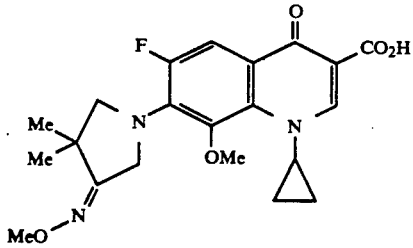

98 mg of the desired product was obtained as colorless powder in the same manner as in Example 2 except that 124 mg (0.33 mmol) of the ketone product obtained in Reference Example 13 was used as the starting material.

Melting point: 208°-212° C.

MS(M/Z): 417(M+), 373, 287.

$^1$H-NMR δ(DMSO-d$_6$) 1.03–1.18(4H,m), 1.29(6H,s), 3.60(2H,s), 3.65(3H,s), 3.79(3H,s), 4.13–4.19(1H,m), 4.34(2H,s), 7.73(1H,s,J=13.8Hz), 8.70(1H,s), 14.93(1H,s).

REFERENCE EXAMPLE 14

5-amino-1-cyclopropyl-6,8-difluoro-1,4-dihydro-7-(4,4-dimethyl-2-aza-6,9-dioxaspiro[4,4]nonan-2-yl)-4-oxoquinoline-3-carboxylic acid

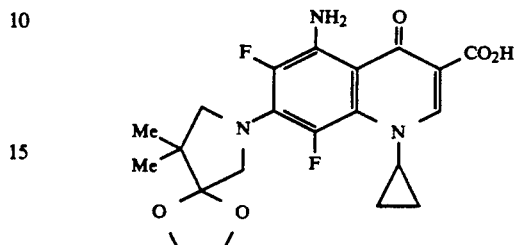

392 mg of the desired product was obtained as yellow powder in the same manner as in Example 3 except that 678 mg (2.5 mmol) of 4,4-dimethyl-2-aza-6,9-dioxaspiro[4,4]nonane trifluoroacetate was used as the starting material.

Melting point: 265°-267° C. (Decomposed).

MS(M/Z): 435(M+).

$^1$H-NMR δ(DMSO-d$_6$): 1.07(10H,brs), 3.60(2H,brs), 3.71(2H,brs), 3.96(4H,s), 7.12(2H,brs), 8.46(1H,s), 14.85(1H,s).

REFERENCE EXAMPLE 15

5-amino-1-cyclopropyl-6,8-difluoro-1,4-dihydro-7-(3,3-dimethyl-4-oxopyrrolidinyl)-4-oxoquinoline-3-carboxylic acid

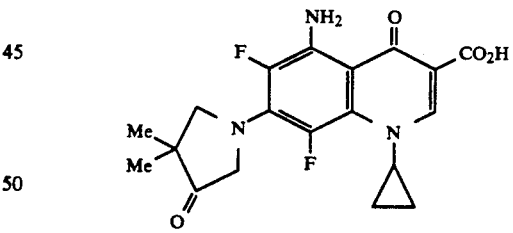

320 mg of the desired product was obtained as yellow powder in the same manner as in Reference Example 13 except that 360 mg of 5-amino-1 cyclopropyl-6,8-difluoro-1,4-dihydro-7-(4,4-dimethyl-2-aza-6,9dioxaspiro[4,4]nonan-2-yl)-4-oxoquinoline-3-carboxylic acid prepared in Reference Example 14 was used.

Melting point: 237°-240° C.

MS(M/Z): 391(M+), 263.

$^1$H-NMR δ(DMSO-d$_6$): 1.08–1.21(4H,m), 1.18(6H,s), 3.82(2H,s), 3.97–4.02(1H,m), 4.12(2H,s), 7.21(2H,brs), 8.24(1H,s), 8.52(1H,s), 14.69(1H,s).

EXAMPLE 20

5-amino-1-cyclopropyl-6,8-difluoro-1,4-dihydro-7-(3-hydroxyimino-4,4-dimethylpyrrolidinyl)-4-oxoquinoline-3-carboxylic acid

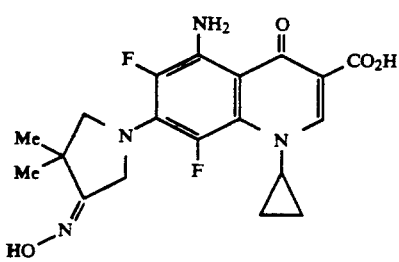

118 mg of the desired product was obtained as yellow powder in the same manner as in Example 2 except that 129 mg (0.33 mmol) of the ketone product obtained in Reference Example 15 and 30 mg of hydroxylamine hydrochloride were used as starting materials.

Melting point: 245°–247° C. (Decomposed).
MS(M/Z): 406(M+), 290, 249.
$^1$H NMR $\delta$(DMSO-d$_6$): 1.08–1.16(4H,m), 1.26(6H,s), 3.62(2H,s), 3.96–4.02(1H,m), 4.38(2H,s), 7.17(2H,brs), 8.50(1H,s), 10.75(1H,s), 14.74(1H,s).

EXAMPLE 21

5-amino-1-cyclopropyl-6,8-difluoro-1,4 dihydro-8-methoxy-7-(3-methoxyimino 4,4-dimethylpyrrolidinyl)-4-oxoquinoline 3-carboxylic acid

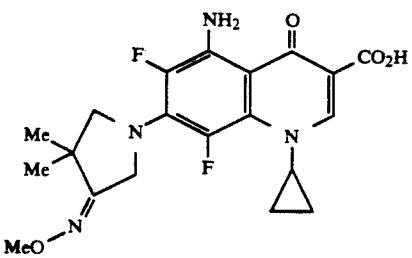

108 mg of the desired product was obtained as yellow powder in the same manner as in Example 2 except that 129 mg (0.33 mmol) of the ketone product obtained in Reference Example 15 was used as the starting material.

Melting point: 236°–239° C. (Decomposed).
MS(M/Z): 420(M+), 290, 249.
$^1$H-NMR $\delta$(DMSO-d$_6$): 1.03–1.18(4H,m), 1.26(6H,s), 3.62(2H,s), 3.82(3H,s), 3.97–4.02(1H,m), 4.38(2H,s), 7.18(2H,brs), 8.47(1H,s), 14.73(1H,s).

TEST EXAMPLE: Antibacterial activities

The antibacterial activities of the compound of the present invention were measured in terms of the minimum inhibitory concentrations (MIC) by an agar plate dilution method in accordance with the standard method of Japan Chemotherapy Association. As a comparative compound, Ofloxancine (OFLX) was used. The results are shown in Table 1.

TABLE 1

| Compound Examples | Test bacteria | | | | | |
|---|---|---|---|---|---|---|
| | a | b | c | d | e | f |
| 1 | ≦0.006 | 0.1 | 0.1 | 0.39 | 0.013 | 0.78 |
| 2 | 0.013 | 0.2 | 0.39 | 1.56 | 0.025 | 1.56 |
| 3 | 0.013 | 0.2 | 0.2 | 0.2 | 0.013 | 6.25 |
| 4 | 0.05 | 0.39 | 0.39 | 0.78 | 0.78 | >12.5 |
| 5 | 0.05 | 0.78 | 0.78 | 1.56 | 0.05 | 25 |
| 6 | 0.025 | 0.39 | 0.2 | 0.78 | 0.025 | 6.25 |
| 7 | 0.025 | 0.78 | 0.39 | 3.13 | 0.05 | 12.5 |
| 8 | ≦0.006 | 0.05 | 0.05 | 0.1 | ≦0.006 | 0.39 |
| 9 | ≦0.006 | 0.1 | 0.1 | 0.39 | 0.013 | 1.56 |
| 10 | ≦0.006 | 0.05 | 0.025 | 0.025 | ≦0.006 | 1.56 |
| 11 | ≦0.006 | 0.2 | 0.1 | 0.1 | 0.013 | 3.13 |
| 12 | 0.013 | 0.2 | 0.1 | 0.2 | 0.025 | 6.25 |
| 13 | ≦0.006 | 0.2 | 0.1 | 0.2 | 0.013 | 3.13 |
| 14 | ≦0.006 | 0.05 | 0.1 | 0.1 | ≦0.006 | 0.39 |
| 15 | <0.006 | 0.05 | 0.1 | 0.78 | <0.006 | 0.78 |
| 16 | <0.006 | 0.05 | 0.05 | 0.05 | <0.006 | 0.78 |
| 17 | <0.006 | 0.05 | 0.05 | 0.2 | <0.006 | 0.78 |
| 18 | 0.013 | 0.2 | 0.2 | 0.39 | 0.025 | 1.56 |
| 19 | 0.013 | 0.2 | 0.2 | 3.13 | 0.05 | 3.13 |
| 20 | ≦0.006 | — | 0.1 | 0.1 | ≦0.006 | 1.56 |
| 21 | 0.013 | — | 0.2 | 0.78 | 0.025 | >50 |
| OFLX | 0.39 | 0.78 | 1.56 | 0.1 | 0.39 | 25 | a: *S. aureus* Smith
b: *S. pyogenes* Cook
c: *E. faecalis* 1373
d: *E. coli* JC-2
e: *S. aureus* JS-1 (MRSA)
f: *S. aureus* KP-90-3 (MRSA)

The oxime derivatives of the present invention were found to have strong antibacterial activities not only against gram positive bacteria such as storeptococcus and enterococcus but also against MRSA.

We claim:

1. An oxime derivative of the formula:

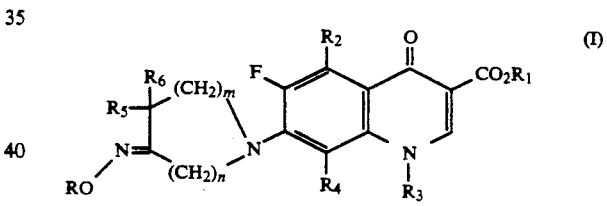

wherein R is a hydrogen atom or a C$_{1-5}$ alkyl group, R$_1$ is a hydrogen atom, a C$_{1-5}$ alkyl group or a carboxyl-protecting group, R$_2$ is a hydrogen atom, a halogen atom, a hydroxyl group or an amino group, R$_3$ is a C$_{3-7}$ cycloalkyl group, R$_4$ is a hydrogen atom, a halogen atom or a C$_{1-4}$ alkoxy group, each of R$_5$ and R$_6$ which may be the same or different, is a hydrogen atom or a C$_{1-5}$ alkyl group, or R$_5$ and R$_6$ together represent a C$_{2-4}$ alkylene group which forms together with the adjacent carbon atom a C$_{3-5}$ ring, provided that when R$_2$ is a hydrogen atom, R$_4$ is a C$_{1-4}$ alkoxy group, m is an integer of 0 or 1, and n is an integer of from 1 to 3; or its pharmaceutically acceptable salt.

2. The oxime derivative according to claim 1, wherein R$_2$ is a hydrogen atom and R$_4$ is a methoxy group in the formula (I); or its pharmaceutically acceptable salt.

3. The oxime derivative according to claim 1, wherein R$_2$ is an amino group, a hydroxy group or an fluorine atom, and R$_4$ is a fluorine atom in the formula (I); or its pharmaceutically acceptable salt.

4. The oxime derivative according to claim 1, which is 1-cyclopropyl-6-fluoro-1,4-dihydro-7-(4-hydroxyimino-1-piperidinyl)-8-methoxy-4-oxoquinoline-3-carboxylic acid of the formula:

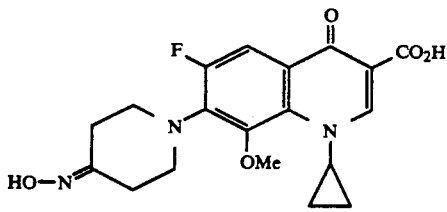

5. The oxime derivative according to claim 1, which is 1-cyclopropyl-6-fluoro-1,4-dihydro-7-(3-hydroxyimini-1-pyrrolidinyl)-8-methoxy-4-oxoquinoline-3-carboxylic acid of the formula:

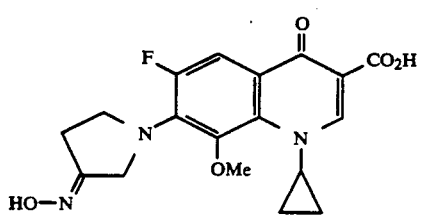

6. The oxime derivative according to claim 1, which is 1-cyclopropyl-6-fluoro-1,4-dihydro-8-methoxy-7-(3-methoxyimino-1-pyrrolidinyl)-4-oxoquinoline-3-carboxylic acid of the formula:

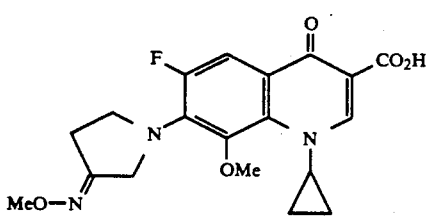

7. The oxime derivative according to claim 1, which is 5-amino-1-cyclopropyl-6,8-difluoro-1,4-dihydro-7-(3-hydroxyimini-1-pyrrolidinyl)-4-oxoquinoline-3-carboxylic acid of the formula:

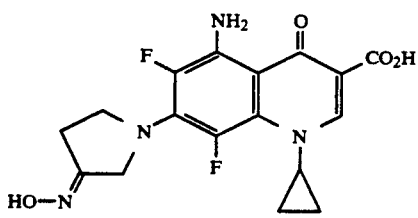

8. The oxime derivative according to claim 1, which is 1-cyclopropyl-6-fluoro-1,4-dihydro-7-(7-hydroxyimino-5-azaspiro[2,4]heptan-5-yl)-8methoxy-4-oxoquinoline-3-carboxylic acid of the formula:

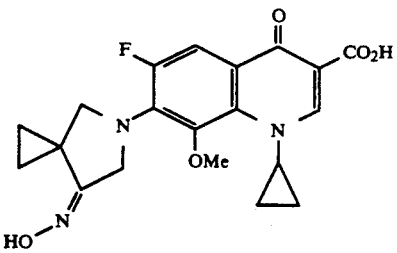

9. The oxime derivative according to claim 1, which is 1-cyclopropyl-6-fluoro-1,4-dihydro-8-methoxy-7-(7-methoxyimino-5-azaspiro[2,4]heptan-5-yl)-4-oxoquinoline-3-carboxylic acid of the formula:

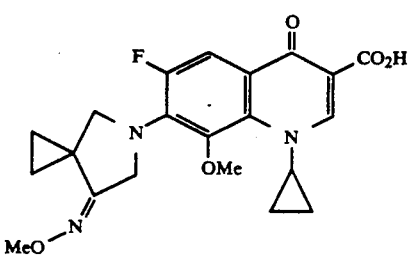

10. The oxime derivative according to claim 1, which is 5-amino-1-cyclopropyl-6,8-difluoro-1,4-dihydro-7-(7-hydroxyimino-5-azaspiro[2,4]heptan-5-yl)-4oxoquinoline-3-carboxylic acid of the formula:

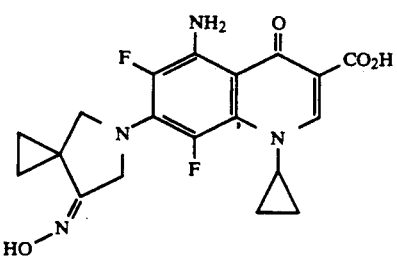

11. The oxime derivative according to claim 1, which is 5-amino-1-cyclopropyl-6,8-difluoro-1,4-dihydro-7-(7-methoxyimino-5-azaspiro[2,4]heptan-5-yl)-4-oxoquinoline-3-carboxylic acid of the formula:

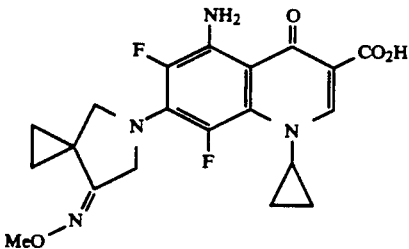

12. An antibacterial agent comprising an antibacterially effective amount of the oxime derivative of the formula (I) as defined in claim 1 or its salt, and a carrier or diluent.

* * * * *